United States Patent
Wong et al.

(10) Patent No.: US 8,318,498 B2
(45) Date of Patent: Nov. 27, 2012

(54) LUMINESCENT PROTEIN STAINING

(75) Inventors: Kwok-Yin Wong, Kowloon (CN);
Dik-Lung Ma, Kowloon (CN);
Wing-Leung Wong, Kowloon (CN);
Wai-Hong Chung, Kowloon (CN);
Fung-Yi Chan, Kowloon (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 919 days.

(21) Appl. No.: 11/907,011

(22) Filed: Oct. 9, 2007

(65) Prior Publication Data
US 2009/0093060 A1  Apr. 9, 2009

(51) Int. Cl.
*G01N 33/68* (2006.01)
*G01N 35/00* (2006.01)

(52) U.S. Cl. .............. 436/43; 436/86; 436/88; 436/164; 436/167; 422/50; 422/504

(58) Field of Classification Search .................. 436/43, 436/86, 88, 164, 167; 422/5, 504
See application file for complete search history.

(56) References Cited

U.S. PATENT DOCUMENTS
6,316,267 B1 * 11/2001 Bhalgat et al. .................. 436/86

OTHER PUBLICATIONS
Lo et al., Synthesis, Photophysical and Electrochemical Properties, and Protein-Binding Studies of Luminescent Cyclometalated Iridium(III) Bipyridine Estradiol Conjugates, Chemistry—A European Journal, vol. 13, Issue 25, p. 7110-7120 (2007).*
Schmid, B. Sythesis and Characterizations of Cyclometalated Iridium(III) Solvento Complexes.(1994). Inorganic Chemistry. 32:9-14.*
Lo et al., Synthesis, Photophysical and Electrochemical Properties, and Protein-Binding Studies of Luminescent Cyctometalated Iridium(III) Bipyridine Estradiol Conjugates, Chemistry—A European Journal, vol. 13, Issue 25, p. 7110-7120 (2007).*

* cited by examiner

*Primary Examiner* — Krishnan S Menon
*Assistant Examiner* — Rebecca M Fritchman
(74) *Attorney, Agent, or Firm* — The Hong Kong Polytechnic University

(57) ABSTRACT

The present invention relates to the use of cyclometalated iridium complexes for detecting poly(amino acids) including peptides, polypeptides, and proteins. Poly(amino acids) are detected in solution, in electrophorectic gels, and on solid supports, including blots. The method of the present invention is rapid, highly sensitive, and extremely facile.

14 Claims, 3 Drawing Sheets

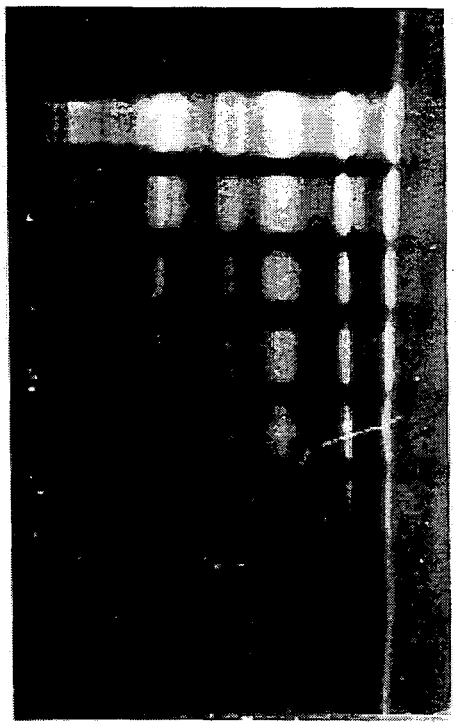
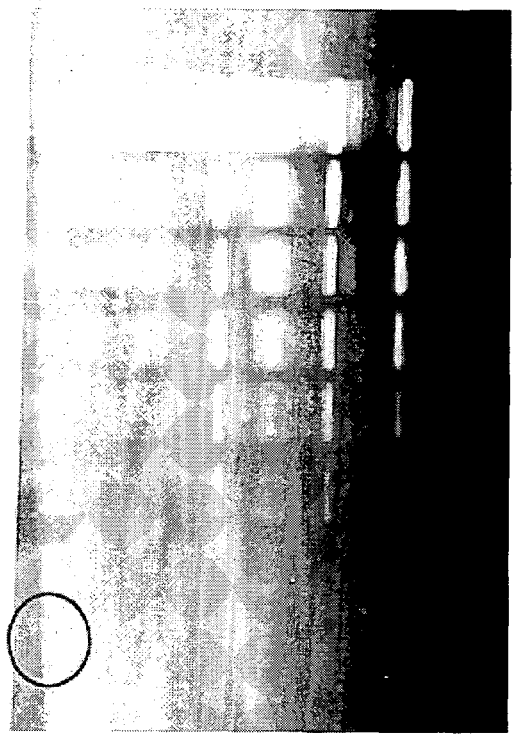
FIG. 2a SYPRO Ru
FIG. 2b Ir staining

LUMINESCENT PROTEIN STAINING

BACKGROUND

Detection and analysis of poly(amino acids) is of great importance in a multitude of diverse activities, ranging from commercial enzyme production, forensics analysis and diagnostics to basic research in biochemistry, molecular biology, neuroscience, developmental biology or physiology. As used herein, a poly(amino acid) is any homopolymer or heteropolymer of amino acids, including peptides and proteins. Primarily, poly(amino acids) are detected and characterized using gel electrophoresis or by solution quantitation assays.

Electrophoresis of poly(amino acids) is most commonly carried out using polyacrylamide gels. Unmodified protein or other poly(amino acid) bands in gels are generally not visible to the naked eye. Thus, for electrophoretic gels to be useful, the bands or spots must be stained, so that they can be localized and identified. Two of the most common methods of staining poly(amino acids) on gels are COOMASSIE Brilliant Blue staining (hereafter referred to as CBB staining) and silver staining.

For CBB staining, the electrophoresis gel is first fixed, stained for several hours with a triphenylmethane-based dye, and then destained for several more hours. The resulting stained gel is pale blue with dark blue bands containing the poly(amino acids). The sensitivity of CBB staining is strongly dependent on how thoroughly the gel is destained. A destaining period of 24 hours typically allows as little as 0.03-0.1 mg of poly(amino acid) to be detected in a single band. However, excessive destaining also results in signal loss from the bands. Although CBB staining is inexpensive, easy to use, and the resulting gels are easily preserved, CBB staining gives linear responses within only a narrow dynamic range. Furthermore, once stained using CBB, the poly(amino acids) in the gel cannot be blotted for immunoanalysis, CBB staining is somewhat selective for poly(amino acid) composition and tends to bind small peptides poorly.

Silver staining utilizes the differential reduction of silver ions bound to the side chains of amino acids in poly(amino acids). For particular poly(amino acids), silver staining is approximately 100- to 1000-fold more sensitive than CBB staining and is capable of detecting 0.1-1.0 ng of poly(amino acid) in a single band. A gel that has been silver stained is clear to yellow-tan, with gray, dark-brown or black poly (amino acid) bands. Silver stained gels can readily preserved, as for CBB stained gels. Like CBB staining, silver staining is time-consuming and yields a narrow linear response for densitometric quantitation. Also, the stained gels cannot be blotted for further analysis. In addition, silver staining requires the handling of several very toxic, unstable and expensive solutions, and the resulting staining is extremely selective for poly(amino acid) composition, both in band color and band intensity. Finally, silver staining requires an exacting methodology that is often difficult to perform reproducibly.

Photoluminescent cyclometalated transition metal complexes have recently been emerged to become a topical area of interest in inorganic photochemistry and phosphorescent materials for optoelectronic and luminescent signaling applications. Significant changes in the photophysical behavior and emission properties of cyclometalated transition metal complexes may be induced by the presence of biomolecules. Luminescent transition metal complexes, such as luminescent ruthenium complex denoted as SYPRO Ruby dye, for protein staining has previously been reported in the literature. The use of luminescent reagents for protein detection offers the possibility of greatly enhanced sensitivity and increased linear quantitation range, while simultaneously increasing the ease of use of the staining reagent.

Styryl dyes sold under the trademark SYPRO Orange and SYPRO Red (Molecular Probes, Eugene, Oreg.) can detect proteins in SDS-polyacrylamide gels using a simple, one-step staining procedure that requires 30 to 60 minutes to complete and does not involve a destaining step. As little as 4-10 ng of protein can routinely be detected with SYPRO Orange or SYPRO Red dyes, rivaling the sensitivity of rapid silver staining techniques and surpassing the best colloidal CBB staining methods available. However, both SYPRO Orange and SYPRO Red dyes require 7% acetic acid in the staining solution, which is problematic when electroblotting, electroelution or measuring enzyme activity is indicated. If acetic acid is not included in the staining solution when using the SYPRO Orange and SYPRO Red stains, proteins may be recovered from gels, but the detection sensitivity obtained with these stains is substantially lower and significant protein-to-protein variability in staining is observed.

Unlike methods using the SYPRO Red and SYPRO Orange styryl dyes, methods using preferred cyclometalated iridium solvento complexes of the present invention do not require the use of organic solvents for optimal staining of proteins, and the cyclometalated iridium complexes are readily soluble and stable in aqueous staining solutions. The cyclometalated iridium complexes of the present invention provide superior staining of proteins in SDS-polyacrylamide gels. Finally, the staining procedure of the present invention is rapid and simple, requires minimal labor, and allows the detection of as little as 1 ng of a poly(amino acid) per band; this sensitivity is in many cases equal to or better than that of rapid silver staining methods, with far less hazard and expense, and is at least an order of magnitude better than CBB staining.

Luminescent sensing of histidine and histidine-rich protein plays a pivotal role in biochemistry and molecular biology, with a special regard to determination which require both temporal and spatial resolution. The abnormal level of histidine-rich proteins are indicator for many diseases, such as advanced liver cirrhosis, AIDS, renal disease, asthma, pulmonary, thrombotic disorders and malaria. Some histidine and histidine-rich proteins analyses have been developed in conjunction with HPLC, capillary electrophoresis, immunoassay and calorimetric detection, etc. However, related studies on luminescent chemosensors for histidine and histidine-rich proteins remain sparse. The cyclometalated iridium complexes of the present invention provide specific staining for histidine-rich proteins in SDS-polyacrylamide gels.

It is an object of the present invention to overcome the disadvantages and problems in the prior art.

DESCRIPTION

The present invention relates to cyclometalated iridium complexes, and their use for the staining and subsequent detection of poly(amino acids), including peptides, polypeptides, and proteins.

These and other features, aspects, and advantages of the apparatus and methods of the present invention will become better understood from the following description, appended claims, and accompanying drawings where:

FIG. 2 shows emissive SDS-PAGE analysis of commercially available low range protein markers with a) SYPRO Orange dye (staining time=30±5 min) as the detecting stain; b) iridium complex (5.0 mg/20 ml, staining time=15±5 min) as the detecting stain.

The following description of certain exemplary embodiment(s) is merely exemplary in nature and is in no way intended to limit the invention, its application, or uses. "Heteroaryl", as used herein, is an aromatic group that contains at least one heteroatom (a non-carbon atom forming part of the ring structure). A heteroaryl substituent is optionally a 5- or 6-membered ring, or is part of a fused 2- or 3-ring structure. A heteroaryl substituent optionally contains one or more heteroatoms, e.g. pyrrolyl, pyridyl, thienyl, or furanyl (single ring, single heteroatom), or oxazolyl, isoxazolyl, oxadiazolyl, or imidazolyl (single ring, multiple heteroatoms), or benzoxazolyl, benzothiazolyl, or benzimidazolyl (mutli-ring, multiple heteroatoms) or quinolyl, benzofuranyl or indolyl (multi-ring, single heteroatom).

Aryl and heteroaryll substituents are typically used to modify the spectral properties, affinity, selectivity, solubility or reactivity of the resulting metal complex, or any combination of these factors. Both aryl and heteroaryl substituents of the instant ligands are independently and optionally substituted as described above for the heteroaromatic rings of the ligands of the invention, including halogen; sulfonic acid or salt of sulfonic acid; phosphonate; phosphate; boronate; alkyl, perfluoroalkyl, or alkoxy; or carboxy, carboxyalkyl, carboxyalkoxy, carboxyalkylamine, or carboxyalkylthio.

Figure 1:
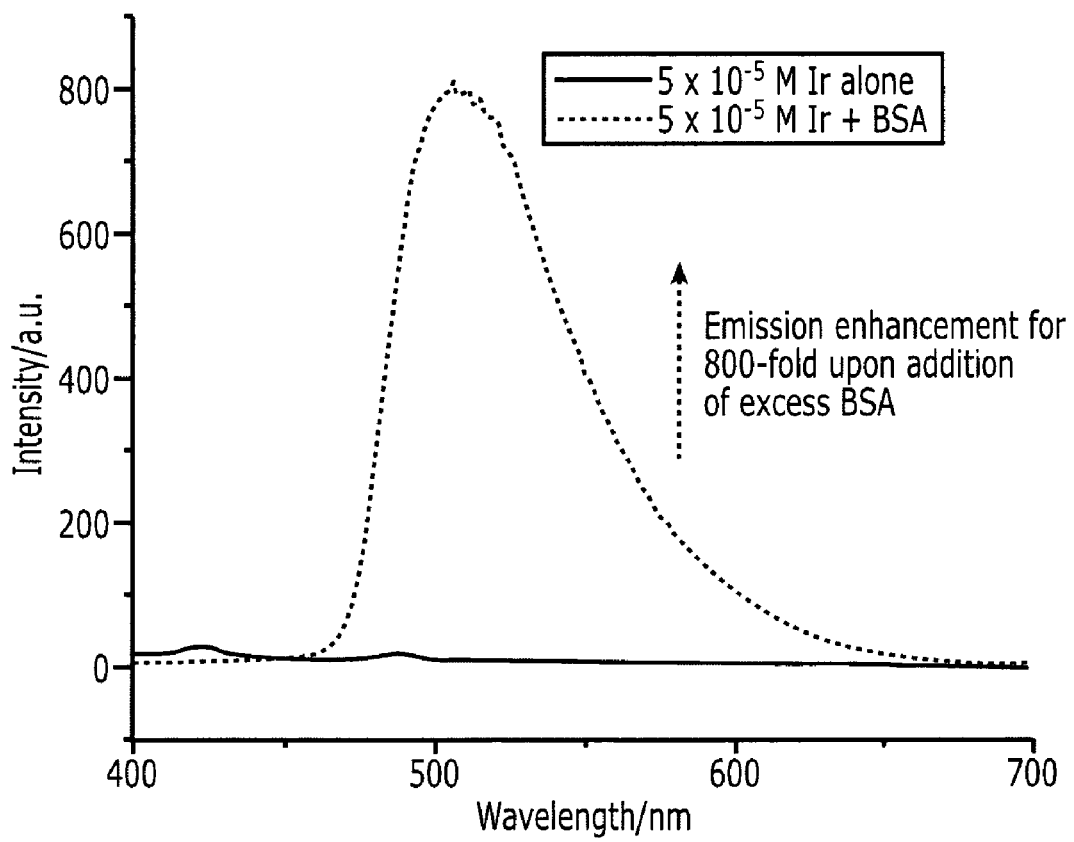
FIG. 1 shows emission spectral traces of 50 µM iridium complex in 10 nM Tris-HCl, pH7.5 buffer with increasing concentration of [BSA]/[Ir]=1000 at 20.0° C.
Figure 3:
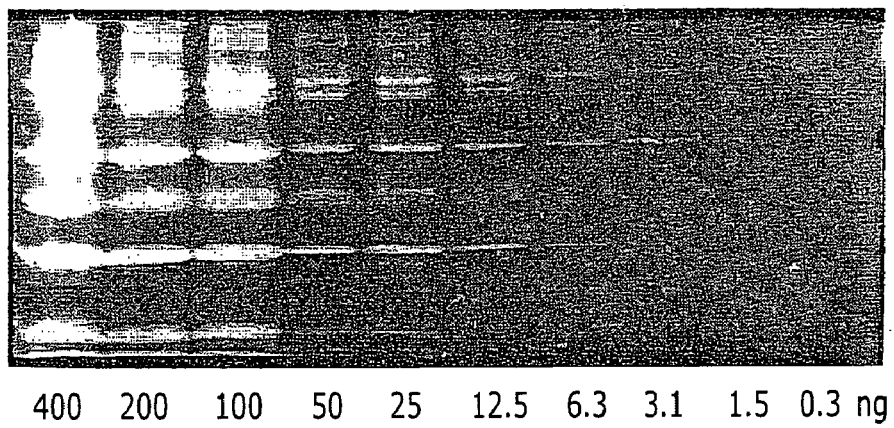
FIG. 3 shows emissive SDS-PAGE analysis of commercially available broad range protein markers with iridium complex (5.0 mg/20 ml, staining time=15±5 min) as the detecting stain.
Figure 4:
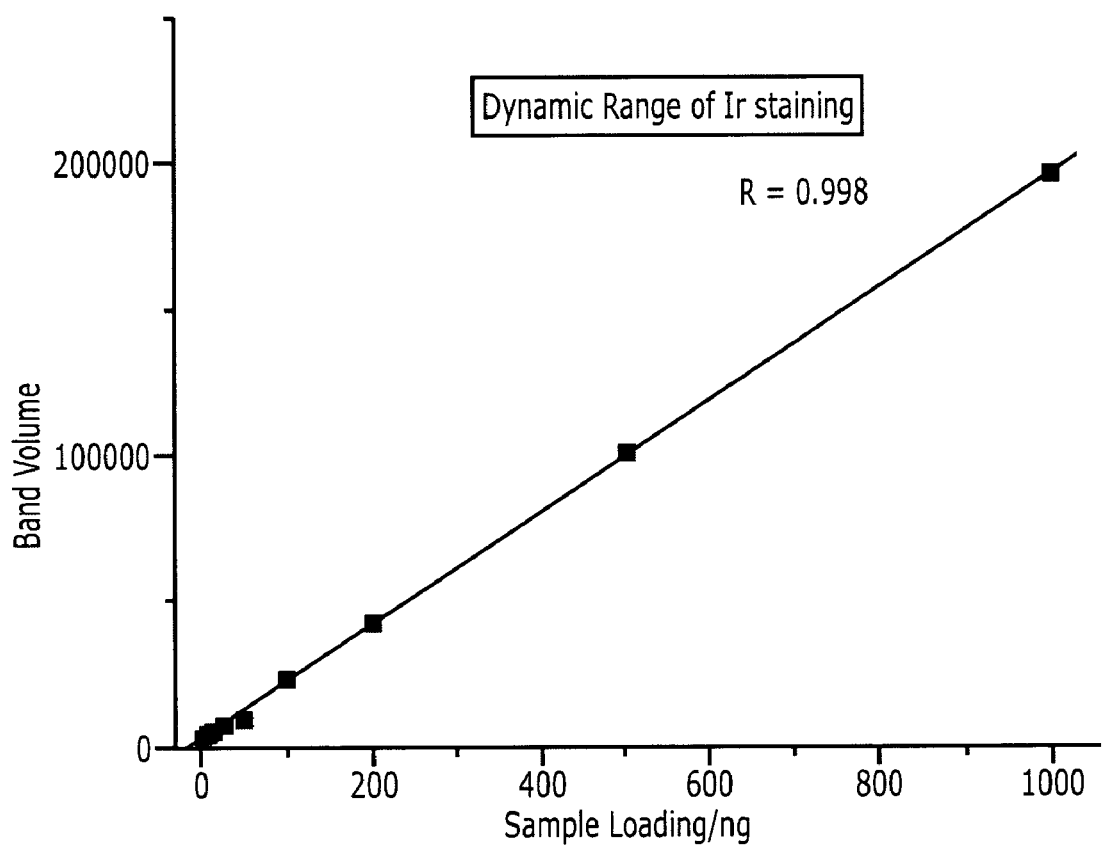
FIG. 4 shows average band volume against sample loading/ng for the proteins (phosphorylose b).

Now, to FIGS. 1-4,

The present invention relates to cyclometalated iridium solvento complexes and their use for the staining and subsequent detection of poly(amino acids), including peptides, polypeptides and proteins. The iridium complex of the present invention, which has low intrinsic luminescence in aqueous medium, associates with peptides and proteins either directly, to yield a strong luminescence. Any poly(amino acid) thereby labeled is capable of being detected with great sensitivity either in solution, in gel electrophoresis, or on solid supports.

The method of the invention utilizes a staining mixture that comprises one or more iridium complexes. The metal ion of the instant invention is an iridium(III) ion, which is capable of binding with any nitrogen donor, carbon donor ligands.

In the embodiments, the iridium complex of the invention is photo-sensitive. The complex is useful for detection of biological important molecules including peptides, polypeptides and proteins luminescence.

The ligands of the invention occupy the coordination sphere of the iridium, and are mono- or polydentate nitrogen donor and/or carbon donor ligands. A ligand that contains at least one nitrogen donor and one carbon donor is an organic moiety that binds to the iridium ion via the donation of 2 electrons from the lone pair of the nitrogen atom and 2 electrons from the carbon atom. To the ligands, the nitrogen atom is typically incorporated into a heteroaromatic ring and the carbon donor is either an aliphatic or aromatic unsaturated organic moiety. Where the ligand possesses a nitrogen donor and a carbon donor for iridium ion binding, it is a bidentate ligand. Typically, the ligands of the invention are bidentate with a nitrogen donor and a carbon donor, which linked by a single covalent bond or by an appropriate covalent linkage at any position.

The iridium ion exhibits an octahedral coordination geometry by binding with two or more ligands, which may be the same or different. Where the iridium ion has an octahedral geometry, the nitrogen and carbon atoms of donor of ligands are oriented around the iridium ion at the vertices of an octahedron, with the iridium ion at the center of the octahedron. The iridium complex is a cyclometalated solvento complex that binding with one or more solvent molecules.

The solvent molecules bound by the iridium ion or the iridium complex of the invention can be water, alcohols such as methanol, ethanol and glycols, ketones such as acetone and acetylacetones, alkylnitriles such as acetonitriles, halogenated alkanes such as dichloromethane and chloroform, ethers such as diethyl ether, the substituted amides such as N,N-dimethylformamides, amines and dimethyl sulfoxides. The coordinated solvent molecules of the iridium complex of the instant invention may be the same or different.

The geometry of a given metal center of the invention exists in three dimensions. As is well known for octahedral metal complexes may exist as a single stereoisomer or a mixture of stereoisomers. The absolute configuration of ligands around the iridium ion does not appear to influence the ability of the complex to be a staining reagent for proteins, peptides and amino acids. Selected examples of the orientation of the iridium complex are shown in Scheme 1.

SCHEME 1

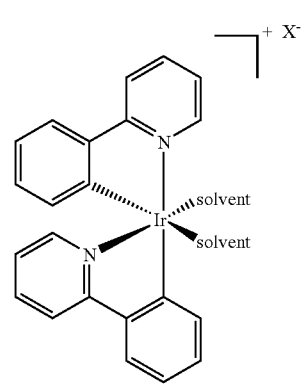

Structure 1

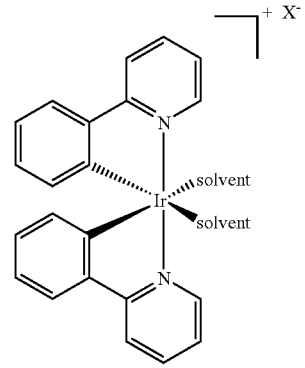

Structure 2

Structure 3

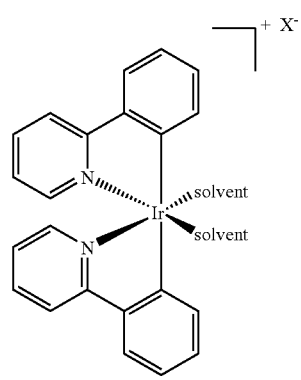

Structure 4

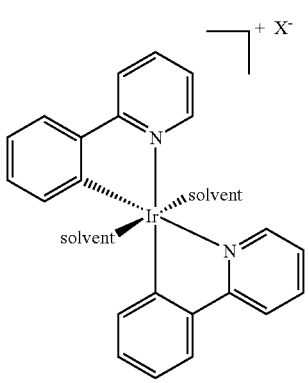

Structure 5

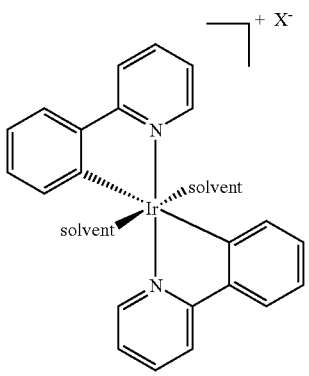

X⁻ can be any anion

The ligands of the instant invention comprises at least one heteroaromatic ring containing a nitrogen atom, through which the ligand binds to the metal atom or ion of the invention. In one embodiment, the ligand comprises two aromatic rings (one heteroaromatic and one homoaromatic) that are linked by a single covalent bond, or by an appropriate covalent linkage. In any embodiment, both of the heteroaromatic and homoaromatic rings of the ligand are optionally substituted by a wide variety of substituents, including alkyl, aryl, and heteroaryl substituents, alkenes, alkynes, halogens, ethers, thioethers, amides, esters, acids, and nitrogen containing groups at any position of the ring, and optionally incorporate with one or more additional heteroatoms that are N, O, or S. Selected examples of the ligand are shown in Scheme 2.

SCHEME 2

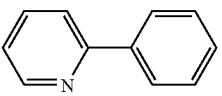
Structure 6

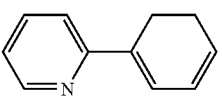
Structure 7

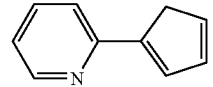
Structure 8

Structure 9

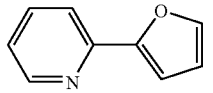
Structure 10

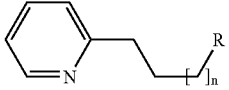
Structure 11

Structure 12

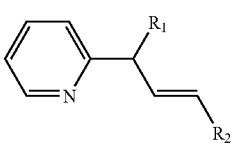
Structure 13

R, R₁, R₂ can be any substituents

The ligands of the instant invention are heteroaromatic nitrogen donor ligand that joined by a single covalent bond or by an appropriate covalent linkage at any position with one or more unsaturated carbon donor groups, which binds to the metal atom or ion of the invention, including the aryl groups, the alkyl groups, heteroaryl groups, cyclo-alkenes and alkynes groups. The carbon donor linking to the aromatic nitrogen donor may not have electron-conjugation with the nitrogen donor. Preferably, the nitrogen donor and carbon donor of the ligand is conjugated electronically.

The carbon donor of the ligand binds to the iridium atom or ion of the invention, as used herein, is a six-membered aromatic ring, joined by a single covalent bond to the heteroaromatric nitrogen donor, which is typically phenyl or substituted phenyl groups.

Additional selected ring substituents may also be utilized to alter the solubility of the resulting iridium complex in either aqueous or organic solvents, to modify the spectral or protein-binding properties of the metal complex, or to modify the electronic environment of the metal center. Typically, the greater the degree of sulfonation on the ligand, the greater the degree of aqueous solubility the resulting metal complex possesses. The additional substitution of ammonium salts, carboxy, carboxyalkyl, carboxyalkoxy, carboxyalkylamino, or carboxyalkylthio or other highly polar substituents also results in enhanced aqueous solubility, improved protein binding or other desirable features.

The nitrogen donor ligands of the invention include pyridines or modified nitrogen containing rings, such as by fusion to aromatic rings. In one embodiment, the ligands of the invention possess at least one pyridyl rings that joined by a single covalent bond with a aryl ring, which is optionally incorporated with one or more additional heteroatoms that are O, or S. Where the pyridyl rings have the primary ring substituents R1, R2, R3 and R4, that are independently selected from H, halogen, CN, alkyl, perfluoroalkyl, or alkoxy having 1-6 carbon atoms; carboxy (—COOH), carboxyalkyl, carboxyalkoxy, carboxyalkylamino, carboxylalkylthio, ammonium salts, amino, salt of amino (where the counterion is a halide, sulfate, sulfonate, phosphate, perchlorate, tetrafluoroborate, tetraphenylboride, or an anion of an aromatic or aliphatic carboxylic acid), alkylamino or dialkylamino. A general chemical structure of the ligand of the instant invention is shown below:

Structure 14

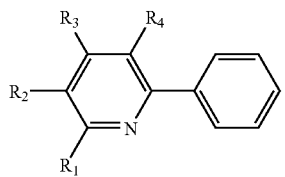

The carbon donor of the ligands, which joined by a single covalent bond or by an appropriate covalent linkage at any position of the nitrogen donor of the heteroaromatic ring, is a fused aromatic ring such as a phenyl ring. The fused aromatic ring substituents, including R1, R2, R3, R4, and R5, are independently and optionally substituted by halogen; sulfonic acid or salt of sulfonic acid; cyano; alkyl, perfluoroalkyl or alkoxy; ammonium salts, amino; alkylamino; dialkylamino; carboxy; or carboxyalkyl, carboxyalkoxy, carboxyalkylamino, or carboxyalkylthio. A general chemical structure of the ligand of the instant invention is shown below:

Structure 15

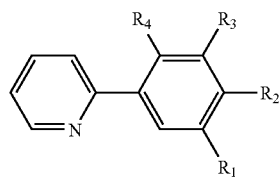

For the ligand of the instant invention, both the aromatic ring with the nitrogen donor and the phenyl ring of the carbon donor are independently and optionally substituted or completely substituted as shown below:

Structure 16

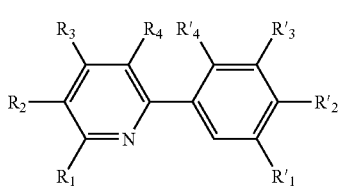

where $R_1$, $R_2$, $R_3$, $R_4$ and $R'_1$, $R'_2$, $R'_3$, $R'_4$ can be any substituent For all embodiments, the ligands on the resulting iridium complex must be coordinated via the nitrogen donors and the carbon donors. The iridium complex of the invention is a cyclometalated solvento complex, which binds with one or more solvent molecules (as defined above) at any position of the metal ion. The net overall charge of the iridium-ligand complex can be neutral or positive with typical anions as the counter-ions. The particularly preferred embodiment of the invention is illustrated graphically in Scheme 1.

The preparation of iridium complexes of such nitrogen donor-carbon donor ligands is well described in the chemical literature. Many ligands suitable for use in the instant invention are commercially available. Where a desired ligand is not readily available, it is often readily prepared by synthetic modification of the ligand prior to complexation with the metal, typically by Suzuki cross-coupling of a pyridyl ring with the suitable aryl rings.

The typical synthesis consists of mixing and heating a solution of the appropriate metal chloride in the presence of the desired nitrogen donor-carbon donor ligand with a desired ligand to metal chloride ratios. The resulting products can be isolated by known methods in the literature. In addition, the chloride ions coordinated in the metal ion are readily displaced with solvents by simple procedures in high yield by following reported articles. A representative example of the preparation of metal complexes with nitrogen donor-carbon donor ligands is reported by Watts et al. (*Inorg. Chem.* 1994, 33, 9-14), incorporated herein by reference.

The present invention utilizes the cyclometalated solvento iridium complexes described above to stain poly(amino acids), followed by detection of the stained poly(amino acids) and optionally their quantification. By poly(amino acid) is meant any assemblage of multiple amino acids, which may be the same or different, that contain peptide linkages. The poly (amino acids) are stained by combining a sample mixture that is thought to contain poly(amino acids), with a staining mixture that comprises one or more cyclometalated iridium complex stain to form a stain-poly(amino acid) complex that gives a detectable luminescent optical response upon illumination. Additional steps are optionally and independently used, in any combination, to provide for separation or purification of the poly(amino acids), for enhancing the detection of the poly(amino acids), or for quantification of the poly(amino acids).

The poly(amino acids) that are suitable for staining using this method include both synthetic and naturally occurring poly(amino acids), such as peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly(amino acids). In one aspect of the invention the poly(amino acids) are enzymes, antibodies, transcription factors, secreted proteins, structural proteins, or binding factors, or combinations thereof. The poly(amino acids) in the sample mixture are optionally covalently or non-covalently bound to a solid surface, such as a glass slide, multi-well plate, microtiter plate well, plastic pin or bead, or semiconductor material, or they are unbound. The staining of a poly(amino acid) that is bound to an analyte on a solid surface indicates the presence of the analyte as well as that of the poly(amino acid).

The poly(amino acids) are optionally unmodified, or have been treated with a reagent so as to enhance or decrease the mobility of the poly(amino acid) in an electrophoretic gel. Such reagents may modify poly(amino acids) by complexing with the peptide (to decrease migration), by cleaving selected peptide bonds (to increase migration of the resulting fragments), by changing the relative charge on the protein (as by phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly (amino acids) having the same original composition, so that the distribution of the dye-poly(amino acid) complex indicates the presence of another analyte.

Although individual amino acids have been labeled using these iridium complex, typically the poly(amino acids) in the sample mixture have a molecular weight greater than about 500 daltons. More typically the poly(amino acids) are more than 800 daltons. Smaller polymers of amino acids (in the <1000 dalton range) are generally difficult to separate from the detergent front on denaturing gels, and typically do not adhere to filter membranes, but are still readily detected in solution. There is no precise upper limit on the size of the poly(amino acids) that may be stained and detected, except that they can not be so bulky that they precipitate out of solution, which also depends in part on the relative hydrophobicity of the poly(amino acid). Furthermore, poly(amino acids) greater than about 200,000 daltons are generally not effectively resolved with current gel technology. The poly (amino acids) present optionally have essentially the same molecular weight or fall within a range of molecular weights. In one embodiment of the invention, the poly(amino acids) present are a mixture of poly(amino acids) of different molecular weights that are used as molecular weight standards. A typical such mixture contains equal mass quantities of myosin, beta-galactosidase, phosphorylase b, bovine serum albumin (BSA), ovalbumin, carbonic anhydrase, trypsin inhibitor, lysozyme and aprotinin. The present invention also efficiently stains low molecular weight peptides, polypeptides and proteins, such as insulin, aprotinin, alpha-bungarotoxin, and a tetramer repeat of the RNA polymerase II C-terminal heptapeptide repeat.

Where the sample mixture is an aqueous solution, the poly(amino acids) of the sample mixture are typically present in a concentration of 10 ng/mL-50 mg/mL, more pretizrably in a concentration of 30 ng/mL-10 mg/mL, most preferably in a concentration of 50 ng/mL-5 mg/mL. Where the sample mixture is an electrophoretic gel, the poly(amino acids) of the sample mixture are typically present in a concentration of 1 ng/band-4 mg/band.

The poly(amino acids) are obtained from a variety of sources; such sources include biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample by mobility (e.g. electrophoretic gel or capillary) or by size (e.g. centrifugation, pelleting or density gradient), or by binding affinity (e.g. to a filter membrane) in the course of the method. In another aspect of the invention, the sample mixture thought to contain the poly(amino acids) has undergone separation. In yet another aspect of the invention, the poly(amino acids) are not separated. Although lipid assemblies such as intact or fragmented biological membranes (e.g. membranes of cells and organelles), liposomes, or detergent micelles, and other lipids are optionally present in the sample mixture; the presence of large amounts of lipids, particularly lipid assemblies, increases background labeling due to non-specific staining. For effective detection of labeled poly(amino acids), intact or fragmented biological membranes in the sample mixture are preferably removed, destroyed or dispersed prior to or in the course of labeling with this method. Typically treatment of the sample mixture by standard methods to remove some or all of such lipids, such as ammonium sulfate precipitation, solvent extraction or trichloroacetic acid precipitation is used. Alternatively or additionally, lipids are removed in the course of labeling the poly(amino acids) such as by electrophoretic separation or other separation techniques (e.g. centrifugation, including gradients), or are disrupted or dispersed below the concentration at which they assemble into micelles (critical micelle concentration) by mechanical means such as sonication. Naturally occurring lipids that are present below their critical micelle concentration are optionally used as a detergent for the purposes of the present invention. Typically, the sample mixture is essentially cell-free. This method is not effective for detecting proteins that remain in cells or are associated with biological membranes.

To make a staining mixture to combine with the sample mixture, the selected iridium complex is typically first dissolved in an organic solvent, such as DMSO, DMF or methanol, usually to a dye concentration of 1-50 mM. This concentrated stock solution is then generally diluted with an aqueous solution according to the assay being performed.

Staining solutions can be stored and reused for months without signal loss. Acetic acid is optionally included in the staining mixture, typically to a concentration of 5-7.5% acetic acid, e.g. to improve labeling of gels relative to that obtained for staining reagents in water. For staining poly(amino acids) on gels or membranes, the iridium complex is diluted into water or buffer.

For luminescence detection, iridium complex concentrations are typically greater than 0.10 mM and less than 50 mM; preferably greater than about 0.20 mM and less than or equal to about 5 mM; more preferably 0.20-3 mM. Although concentrations below and above these values likewise result in detectable staining for certain poly(amino acids), depending on the sensitivity of the detection method, iridium complex concentrations greater than about 10 mM generally lead to quenching of the luminescence signal.

A particular staining reagent is generally selected for a particular assay using one or more of the following criteria: sensitivity to poly(amino acids), dynamic range, photostability, staining time, and insensitivity to the presence of nucleic acids. The sensitivity and dynamic range of the iridium complex is determined using the procedures of Example 9. Preferably, the staining reagent of the present invention have a sensitivity of 1-2 ng or less of poly(amino acid) per band in electrophoretic gels. The preferred staining reagent of the present invention have a dynamic range of about 3 or more orders of magnitude of poly(amino acid) concentration.

The preferred staining reagent in an aqueous solution in combination with poly(amino acids), exhibit a luminescence enhancement that is preferably greater than 800-fold relative to the iridium complex in the absence of poly(amino acids). Finally, the preferred staining reagents of the invention have a molecular weight of 500-1500 grams per mole.

The staining mixture is combined with the sample mixture in such a way as to facilitate contact between any staining reagent and any poly(amino acids) present in the combined mixture.

Destaining of stained gels is typically not necessary for luminescent detection of proteins using the iridium complexes of the invention, although for certain staining formulations containing methanol/acetic acid, destaining typically improves poly(amino acid) detection in gels. For example, while staining of proteins in polyacrylamide gels is typically accompanied by some background staining of the gel matrix, such background staining can be reduced by incubation of the stained gel in a comparable formulation comprising an acid and an alcohol that does not contain the staining iridium complex. This incubation typically removes staining reagent from the gel background, with little loss of protein staining. Stained gels may also be washed briefly after staining to prevent transfer of the staining iridium complex to other surfaces. The duration of staining is such that stained gels can be photographed months after staining without significant loss of signal.

Electrophoretic gels stained according to the method of the invention can subsequently be dried onto filter paper or between plastic sheets (e.g. cellophane), using standard procedures.

The method of the present invention optionally further comprises one or more additional reagents that are simultaneously or sequentially combined with the sample mixture, the staining mixture, or the combined mixture. An additional reagent is optionally a detection reagent that colocalizes with poly(amino acids) in general or with specific poly(amino acids) to enhance the detection thereof by the method of the present invention. Alternatively, the additional reagent is useful for identification of other components in the sample mixture, such as a nucleic acid stain, or a stain for lipids or carbohydrates. Or, the additional reagent is a detection reagent designed to interact with a specific portion of the sample mixture, so as to probe for a specific component of the sample mixture, where spatial coincidence of the iridium complex and the detection reagent indicates that the additional reagent is also associated with the poly(amino acids).

The additional reagent also incorporates a means for producing a detectable response. A detectable response means a change in, or occurrence of, a parameter in a test system that is capable of being perceived, either by direct observation or instrumentally. Such detectable responses include the change in, or appearance of, color, fluorescence, reflectance, pH, chemiluminescence, infrared spectra, magnetic properties, radioactivity, light scattering, x-ray scattering, or the precipitation of an electron-rich substrate. Appropriate labels to provide a detectable response include, but are not limited to, a visible or fluorescent dye, a chemiluminescent reagent, an enzyme substrate that produces a visible or fluorescent precipitate upon enzyme action (for example, the action of horseradish peroxidase upon diaminobenzidine, or enzyme action on a labeled tyramide), visible or fluorescent labeled microparticles, a metal such as colloidal gold, or a silver-containing reagent, or a signal that is released by the action of light upon the reagent (e.g. a caged fluorophore that is activated by photolysis, or the action of light upon diaminobenzidine).

The detectable label of the additional reagent is detected simultaneously or sequentially with the optical signal of the iridium complexes of the present invention.

In one embodiment of the invention, the additional dye(s) colocalize with the iridium complex such that the labeling of some or all poly(amino acids) exhibits quenching. Alternatively, the additional reagent is another protein stain (such as CBB or silver stain) such that labeling of the poly(amino acids) is enhanced by the colocalization of staining.

Other useful additional reagents are fluorescent nucleic acid stains. A variety of appropriate nucleic acid stains are known in the art, including but not limited to, thiazole orange, ethidium homodimer, ethidium bromide, propidium iodide, HOECHST 33258, and DAPI. Additional useful nucleic acid stains are described in the international applications WO 93/06482, DIMERS OF UNSYMMETRICAL CYANINE DYES or WO 94/24213, CYCLIC SUBSTITUTED UNSYMMETRICAL CYANINE DYES; U.S. Pat. Nos. 5,321,130 or 5,410,030, all incorporated herein by reference. The use of an appropriate nucleic acid stain in conjunction with the dyes of the present invention can be selected to allow simultaneous or sequential observation of poly(amino acids) and nucleic acids such as DNA and RNA.

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

EXAMPLES

Synthesis of the Metal Complex

Step 1: To a solution of Iridium(III) trichloride hydrated (0.60 g, 2 mmol) in 10 mL D.I. water and 20 mL of 2-(2-methoxyethoxy)ethanol, 2-phenyloyridine (0.64 g, 4.1 mmol) was added. The resulting mixture was reacted at 120° C. for 10 h. The reaction mixture was cooled in an iced bath and iced water (50 mL) was added. The precipitates were collected by filtration and washed with D.I. water. After drying, the yellow solid was obtained with 90% yield (0.96 g).

Step 2: The yellow solid (0.53 g, 0.5 mmol) was dissolved in 20 mL of methanol and a solution of AgOTf (0.283 g, 1.1 mmol) in 10 mL of methanol was added. The mixture was stirred at 40° C. for 2 h. After cool down to room temperature, the precipitates were filtered through Celite and the filtrate was evaporated to dryness to yield a yellow, oily residue. This residue was washed with diethylether and dried under vacuum to yield a hardened solid material. The material was collected and dried for an additional 16 h under vacuum to yield the final product with 95% yield (0.65 g).

Sample Mixture

The sample mixture is a solid, paste, emulsion or solution that contains or is suspected to contain poly(amino acids).

The sample mixture is an aqueous solution, typically prepared with water (e.g. pure proteins) or aqueous buffer, or is combined with an aqueous solution in the course of labeling. By aqueous solution is meant a solution that is predominantly water and retains the solution characteristics of water. Where the solution contains solvents in addition to water, water is the predominant solvent.

Luminescence Emission Spectra and Luminescence Enhancement of Selected Iridium Complex Stains in Solution Measurements are performed using 50 µM iridium complex+50 mM BSA in 10 mM Tris-HCl, pH 7.5 with a 3.0 mL sample volume. Fluorescence enhancements are calculated at emission maxima in a standard fluorometer using 350 nm excitation. See FIG. 1.

Staining of Low-Range Molecular Weight Protein Standards

SDS-polyacrylamide gel electrophoresis is performed by standard methods utilizing 4% T, 2.6% C stacking gels, pH 6.8 and 15% T, 2.6% C separating gels, pH 8.8. % T is the total monomer concentration expressed in grams per 100 mL and % C is the percentage crosslinker. A staining solution of iridium complex is prepared by diluting a solution that contain 5.0 mg of iridium complex in 0.5% methanol of DI $H_2O$ (20 mL), pH 7.0 with vigorous mixing. Alternatively, a wide range of buffers are compatible with staining, including but not limited to formate, pH 4.0; citrate, pH 4.5; acetate, pH 5.0; MES, pH 6.0; imidazole, pH 7.0; HEPES, pH 7.5; Tris acetate, pH 8.0; Tris-HCl, pH 8.5; Tris borate, 20 mM EDTA, pH 9.0; and bicarbonate, pH 10.0. Approximately 20-25 mL of staining solution is used for a typical mini-gel (5 cm×9 cm×1 mm). The gel is placed into the staining solution and the container is covered with aluminum foil to protect the dye from bright light. The gel is gently agitated for at least 15 minutes at room temperature using an orbital shaker (50: RPM). After staining, the gel is briefly dipped in water and visualized on a UV light box. Regardless of the buffer, proteins stained using iridium complex are visualized as bright green bands. As little as 1.5 ng of protein may be visualized when the fluorescent image is recorded by photography using a 300 nm UV transilluminator. Parallel experiments performed using SYPRO Orange dye reveal similar detection sensitivities when staining is conducted in 7% acetic acid, but inferior performance in the phosphate buffer. In the latter buffer, protein bands are barely detectable above background fluorescence with these latter dyes. See FIG. 2.

Staining of Broad-Range Molecular Weight Protein Standards

SDS-polyacrylamide gel electrophoresis is performed by standard methods utilizing 4% T, 2.6% C stacking gels, pH 6.8 and 15% T, 2.6% C separating gels, pH 8.8. % T is the total monomer concentration expressed in grams per 100 mL and % C is the percentage crosslinker. A staining solution of iridium complex is prepared by diluting a solution that contain 5.0 mg of iridium complex in 0.5% methanol of DI $H_2O$ (20 mL), pH 7.0 with vigorous mixing. Alternatively, a wide range of buffers are compatible with staining, including but not limited to formate, pH 4.0; citrate, pH 4.5; acetate, pH 5.0; MES, pH 6.0; imidazole, pH 7.0; HEPES, pH 7.5; Tris acetate, pH 8.0; Tris-HCl, pH 8.5; Tris borate, 20 mM EDTA, pH 9.0; and bicarbonate, pH 10.0. Approximately 20-25 mL of staining solution is used for a typical mini-gel (5 cm×9 cm×1 mm). The gel is placed into the staining solution and the container is covered with aluminum foil to protect the dye from bright light.

The gel is gently agitated for at least 15 minutes at room temperature using an orbital shaker (50:RPM). After staining, the gel is briefly dipped in water and visualized on a UV light box. Regardless of the buffer, proteins stained using iridium complex are visualized as bright green bands. As little as 1.5 ng of protein may be visualized when the fluorescent image is recorded by photography using a 300 nm UV transilluminator.

Staining of Histidine-Rich Proteins

The histidine-rich proteins are separated by SDS-polyacrylamide gel electrophoresis utilizing a 4% T, 2.6% C stacking gel, pH 6.8 and 15% T, 2.6% C separating gel, pH 8.8 according to standard procedures. A staining solution of iridium complex is prepared by diluting a solution that contain 5.0 mg of iridium complex in 0.5% methanol of DI $H_2O$ (20 mL), pH 7.0 with vigorous mixing. Alternatively, a wide range of buffers are compatible with staining, including but not limited to formate, pH 4.0; citrate, pH 4.5; acetate, pH 5.0; MES, pH 6.0; imidazole, pH 7.0; HEPES, pH 7.5; Tris acetate, pH 8.0; Tris-HCl, pH 8.5; Tris borate, 20 mM EDTA, pH 9.0; and bicarbonate, pH 10.0. Approximately 20-25 mL of staining solution is used for a typical mini-gel (5 cm×9 cm×1 mm). The gel is placed into the staining solution and the container is covered with aluminum foil to protect the dye from bright light. The gel is gently agitated for at least 15 minutes at room temperature using an orbital shaker (50:RPM). After staining, the gel is briefly dipped in water and visualized on a UV light box. Regardless of the buffer, proteins stained using iridium complex are visualized as bright green bands. As little as 1.5 ng of protein may be visualized when the fluorescent image is recorded by photography using a 300 nm UV transilluminator.

Detection of Proteins in Non-Denaturing Polyacrylamide Gels

A dilution series of the proteins of interest is prepared in Native Gel Loading Buffer (125 mM Tris-HCl, pH 6.8, 10% glycerol and 0.015% bromophenol blue). The samples are loaded onto a Tris-HCl nondenaturing polyacrylamide gel, and the gel is electrophoresed under standard conditions. The electrophoresed gel is stained and photographed as described above.

Detection of Proteins in Sodium Dodecyl Sulfate (SDS)-Polyacrylamide Gels (with Destaining)

The proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. A staining solution of iridium complex is prepared by diluting a solution that contain 5.0 mg of iridium complex in 0.5% methanol of DI $H_2O$ (20 mL), pH 7.0 with vigorous mixing. The gel is placed into the staining solution and the container is covered with aluminum foil to protect the dye from bright light. The gel is gently agitated for at least 15 minutes at room temperature using an orbital shaker (50:RPM). Inspection of the gel using a hand held midrange UV light source indicates that the entire gel is stained. The gel is subsequently transferred to a destaining solution of 30% methanol, 7% acetic acid and is incubated for an additional 4-6 hours. At this point protein stains are eluted from the polyacrylamide matrix but selectively retained on the proteins within the matrix. The gel is viewed using a 300 nm UV transilluminator. Proteins appear as green luminescent bands.

Detection of Proteins in Sodium Dodecyl Sulfate (SDS)-Polyacrylamide Gels (without Destaining)

The proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. A staining solution of iridium complex is prepared by diluting a solution that contain 5.0 mg of iridium complex in 0.5% methanol of DI $H_2O$ (20 mL), pH 7.0 with vigorous mixing. The gel is placed into the staining solution and the container is covered with aluminum foil to protect the dye from bright light. The gel is gently agitated for at least 15 minutes at room temperature using an orbital shaker (50:RPM). Gels are rinsed in DI $H_2O$ for 10-15 minutes and viewed using a 300 nm UV transilluminator. Proteins appear as green luminescent bands on a clear background.

Staining Protein Gels with Iridium Complex Stains in the Running Buffer

The proteins of interest are prepared for loading on standard SDS gels, using standard methods. Dilution series of known molecular weight markers, or proteins of unknown concentration, or protein mixtures of unknown composition are used. The gels are loaded and run under standard conditions, excepting that the running buffer contains 0.20-3 mM of iridium complex. The stained gels are either photographed directly after electrophoresis or are destained in 7.5% acetic acid or phosphate-buffered saline for 20-50 minutes to remove background staining prior to photography. The sensitivity obtained using this procedure is about the same as that obtained by staining gels after electrophoresis. In addition, the migration of protein bands can be monitored through the glass plates that support the gel, during electrophoresis.

Pre-Staining of Proteins Prior to Electrophoresis

The proteins of interest are diluted to appropriate concentrations in electrophoresis sample buffer. The samples are then heated to 90-95° C. for 4-5 minutes and allowed to cool to room temperature. Iridium complex is added to the protein solutions to a final concentration of 0.20-3 mM, and the samples are loaded onto a 12% polyacrylamide gel, or other appropriate percentage gel. The gel is electrophoresed under standard conditions and visualized directly using ultraviolet illumination. The sensitivity of this method is somewhat less than the sensitivity possible using the methods of post staining the gel after electrophoresis.

Quantitation of Protein Concentration in Gel

The proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. A staining solution of iridium complex is prepared by diluting a solution that contain 5.0 mg of iridium complex in 0.5% methanol of DI $H_2O$ (20 mL), pH 7.0 with vigorous mixing. The gel is placed into the staining solution and the container is covered with aluminum foil to protect the dye from bright light. The gel is gently agitated for at least 15 minutes at room temperature using an orbital shaker (50:RPM). Gels are rinsed in DI $H_2O$ for 10-15 minutes and viewed using a 300 nm UV transilluminator. Instrument software provides digital values corresponding to the luminescence intensity of the signal in each band. The luminescence intensity values obtained are used to determine protein concentrations by comparison to signals obtained using a dilution series of known concentrations prepared using either the same protein or a protein standard, such as BSA. Staining solution of iridium complex exhibits a linear luminescence detection range of about 1.5-1000 ng of phosphorylase by using these procedures. Greater sensitivity or dynamic range is possible upon optimization of assay conditions. See FIG. 4.

Detection of Proteins in Gels Using a CCD Camera

Proteins in polyacrylamide gels are stained as described in example 2. Stained material is placed on the UV-transilluminator of a CCD camera-based imaging workstation such as a Boehringer-Mannheim Lumi-Imager (Boehringer-Mannheim, Indianapolis, Ind.), Genomic Solutions BioImage (Genomic Solutions, Ann Arbor, Mich.) or Bio-Rad Fluor-S system (Bio-Rad, Hercules, Calif.). All units provide excitation illumination of about 300 nm. 600+/−30 nm band pass emission filters are used with the Lumi-Imager and BioImage systems while a 520 nm long pass emission filter is used with the Fluor-S. Images of gels are captured utilizing standard software-driven procedures provided by each manufacturer. Proteins appear as white bands on a gray to black background or as black bands on light gray to white background on the computer monitor depending upon the display mode selected. Instrument software provides digital values corresponding to the luminescence intensity of the signal in each band.

Detection of Proteins on Filter Membranes Following Dot-blotting or Western Transfer The protein of interest is diluted in TBS (20 mM Tris-HCl, pH 7.5, 500 mM NaCl), then applied directly to a PVDF or nitrocellulose filter membrane. The membrane is washed once with TBS, allowed to air dry and then is floated face down in a solution containing 5.0 mg of iridium complex in 0.5% methanol of DI $H_2O$ (20 mL), pH 7.0 with vigorous mixing. Alternatively, the proteins are first separated by gel electrophoresis and transferred to a PVDF or nitrocellulose filter membrane using standard procedures. The blot is allowed to dry completely, and is then stained by placing it face down in staining solution as described above. The blots are rinsed in DI $H_2O$ for 10-15 minutes and viewed using a 300 nm UV transilluminator.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method for detecting any types of poly(amino acid) in a mixture, comprising the steps of:
   combining a first mixture with a staining mixture containing at least one cyclometalated iridium complex which is covalently bonded to one or more of nitrogen donor ligands and/or carbon donor ligands, and covalently bonded to one or more solvento ligands;
   incubating said combined mixture;
   illuminating said combined mixture; and
   observing said detectable optical response,
   wherein the solvento ligands can be one or more selected from the group consisting of water, alcohols, ketones, alkynitriles, halogenated alkanes, ethers, substituted amides, and dimethyl suloxides.

2. The method for detecting any types of poly(amino acid) in claim 1, wherein cyclometalated iridium incorporates an iridium (III) ion into a heteroaromatic ring.

3. The method of detecting any types of poly(amino acid) in claim 1, wherein said ligands can be monodentate, bidentate, or polydentate ligands.

4. The method of detecting any types of poly(amino acid) in claim 1, wherein said cyclometalated iridium further comprises one or more counter ions selected from the group consisting of halide, sulfate, sulfonate, phosphate, perchlorate, tetrafluoroborate, tetraphenylboride, anion of aromatic carboxylic acid, and aliphatic of carboxylic acid.

5. The method of detecting any types of poly(amino acid) of claim 1, wherein said nitrogen donor ligands can be at least one pyridyl ring containing substituents selected from the group consisting of H, a halogen, CN, alkyl, perfluoroalkyl, alkoxy, carboxy, carboxyalkyl, carboxyalkoxy, carboxalkyl amino, carboxylalkylthio, ammonium salts, amino, salt of amino, alkylamino, and dialkylamino.

6. The method of detecting any types of poly(amino acid) of claim 1, wherein said cyclometalated iridium is selected from the group consisting of:

Structure 1

Structure 2

Structure 3

Structure 4

Structure 5

$X^-$ can be any anion

7. The method of detecting any types of poly(amino acid) of claim 1, further comprising the step of quantifying said poly(amino acid) by measuring said detectable optical response and comparing said measurement with a standard.

8. The method of detecting any types of poly(amino acid) of claim 1, wherein said first mixture is present on a solid or semi-solid matrix.

9. The method of detecting any types of poly(amino acid) of claim 1, wherein said first mixture is present on or in an electrophoresis medium.

10. The method of detecting any types of poly(amino acid) in claim 1, further comprising analyzing the poly(amino acid) by mass spectrometry.

11. The method of detecting any types of poly(amino acid) in claim 1, further comprising adding an additional reagent to said first mixture, said staining mixture, or said combined mixture.

12. The method of detecting any types of poly(amino acid) in claim 1, further comprising electrophoretically separating said first mixture before or after it is combined with said staining mixture.

13. The method of detecting any types of poly(amino acid) in claim 1, wherein the steps can be automated.

14. The method of detecting any types of poly(amino acid) in claim 1, wherein the staining mixture is able to distinguish histidine containing biomolecules and histidine-rich poly(amino acid) through detectable optical response.

* * * * *